(12) United States Patent
Schumacher et al.

(10) Patent No.: US 7,914,557 B2
(45) Date of Patent: Mar. 29, 2011

(54) ORTHOPEDIC FIXATION DEVICE AND ORTHOPEDIC FIXATION SYSTEM

(75) Inventors: Joerg Schumacher, Tuttlingen (DE); Ulrich Kramer, Oberwangen (CH); Stephan Lindner, Tuttlingen (DE); Jens Beger, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 783 days.

(21) Appl. No.: 11/801,899

(22) Filed: May 10, 2007

(65) Prior Publication Data

US 2008/0021467 A1    Jan. 24, 2008

Related U.S. Application Data

(63) Continuation of application No. PCT/EP2005/011455, filed on Oct. 26, 2005.

(30) Foreign Application Priority Data

Nov. 12, 2004   (DE) .......................... 10 2004 056 091

(51) Int. Cl.
*A61B 17/70* (2006.01)
(52) U.S. Cl. ...................................... 606/246
(58) Field of Classification Search .......... 606/246–279; A61B 17/70
See application file for complete search history.

(56) References Cited

U.S. PATENT DOCUMENTS

| | | | | |
|---|---|---|---|---|
| 5,611,800 | A * | 3/1997 | Davis et al. ................... | 606/250 |
| 6,001,098 | A | 12/1999 | Metz-Stavenhagen et al. | |
| 6,183,473 | B1 * | 2/2001 | Ashman ....................... | 606/278 |
| 6,413,257 | B1 | 7/2002 | Lin et al. | |
| 7,591,838 | B2 * | 9/2009 | Kramer et al. ................ | 606/265 |
| 2002/0143332 | A1 * | 10/2002 | Lin et al. ..................... | 606/61 |
| 2003/0093077 | A1 | 5/2003 | Schläpfer et al. | |
| 2004/0010253 | A1 * | 1/2004 | Morrison ...................... | 606/61 |
| 2005/0131404 | A1 * | 6/2005 | Mazda et al. ................. | 606/61 |
| 2006/0004359 | A1 | 1/2006 | Kramer et al. | |
| 2006/0004360 | A1 * | 1/2006 | Kramer et al. ................ | 606/61 |

FOREIGN PATENT DOCUMENTS

| | | |
|---|---|---|
| EP | 0 314 021 A2 | 5/1989 |
| EP | 0 524 441 | 1/1993 |
| EP | 0 695 538 B1 | 10/1999 |
| EP | 10 16 381 A1 | 7/2000 |
| WO | WO 01/52758 A | 1/2001 |
| WO | WO 01/78613 A | 10/2001 |
| WO | WO 02/053038 A2 | 7/2002 |
| WO | PCT/EP02/09878 * | 9/2002 |
| WO | WO 2004/021901 A | 3/2004 |
| WO | WO 2004/021902 A1 | 3/2004 |

* cited by examiner

*Primary Examiner* — Eduardo C Robert
*Assistant Examiner* — Summer L Kostelnik
(74) *Attorney, Agent, or Firm* — RatnerPrestia

(57) ABSTRACT

In order to improve an orthopedic fixation device for connecting a first anchoring element (12) which has a connecting section (26) and can be anchored in or on a bone (18) to a connecting element (14) which can be connected to a second anchoring element which can be anchored in or on a bone, wherein the fixation device is movable relative to the connecting element and to the anchoring element in an adjusting position and can be secured on the connecting element and on the anchoring element in a fixing position, such that the connecting element can be secured on the anchoring element in a particularly simple manner it is suggested that a single tensioning member (50; 122; 166; 172) which is supported so as to be movable be provided for transferring the fixation device from the adjusting position into the fixing position and vice versa.

30 Claims, 12 Drawing Sheets

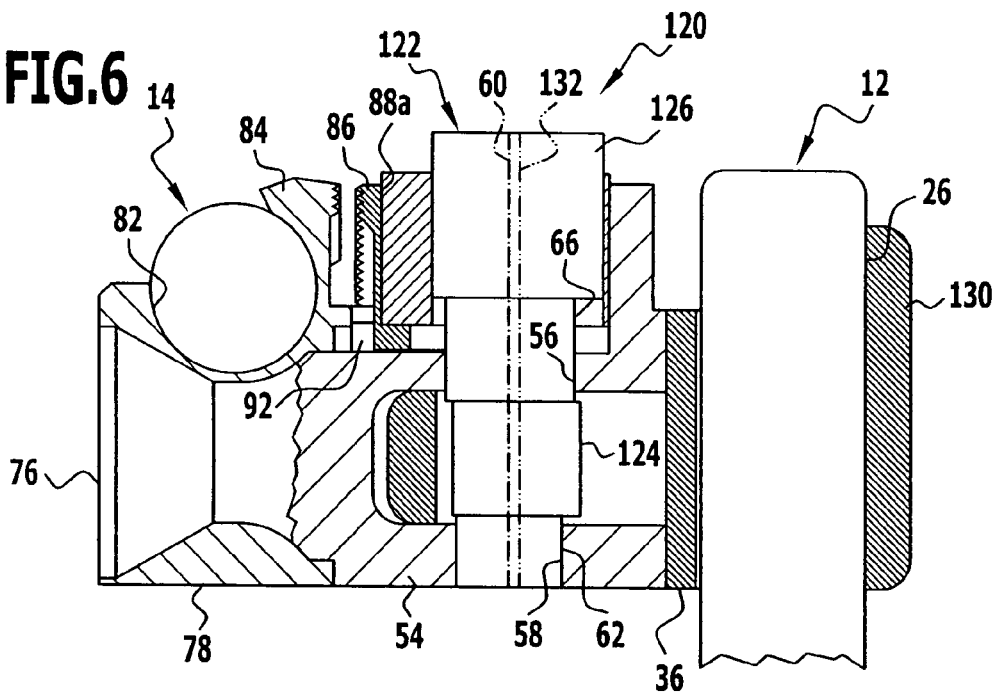
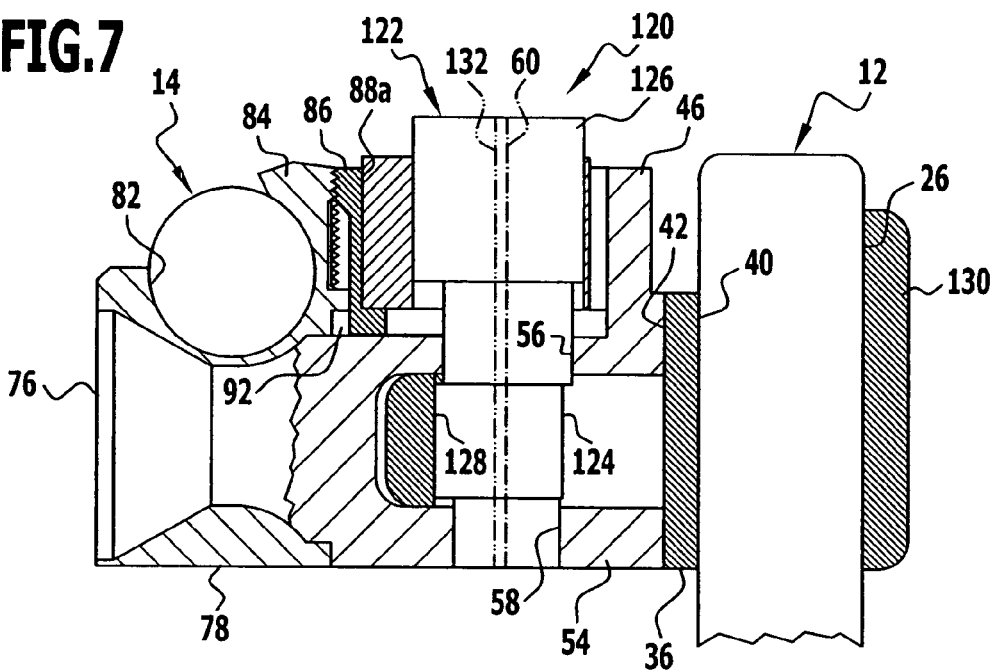

ORTHOPEDIC FIXATION DEVICE AND ORTHOPEDIC FIXATION SYSTEM

This application is a continuation of International application No. PCT/EP2005/011455 filed on Oct. 26, 2005.

The present disclosure relates to the subject matter disclosed in International application No. PCT/EP2005/011455 of Oct. 26, 2005 and German application No. 10 2004 056 091.9 of Nov. 12, 2004, which are incorporated herein by reference in their entirety and for all purposes.

BACKGROUND OF THE INVENTION

The invention relates to an orthopedic fixation device for connecting a first anchoring element, which has a connecting section and can be anchored in or on a bone, to a connecting element which can be connected to a second anchoring element which can be anchored in or on a bone, wherein the fixation device is movable relative to the connecting element and to the anchoring element in an adjusting position and can be secured on the connecting element and on the anchoring element in a fixing position.

Furthermore, the invention relates to an orthopedic fixation system comprising at least two anchoring elements which can be anchored in or on a bone, at least one connecting element for connecting the at least two anchoring elements and at least one orthopedic fixation device for connecting the at least one connecting element to a connecting section of one of the at least two anchoring elements.

Orthopedic fixation devices and fixation systems such as those described at the outset are used to position and fix different bones or bone fragments in place relative to one another. For this purpose, anchoring elements in the form of bone screws or bone hooks are normally inserted into the respective bone fragments and connected permanently or temporarily by means of a connecting element which is secured to both anchoring elements. Fixation devices are known, with which the connecting element can be secured on the anchoring element laterally offset in relation to the connecting section. The connection between anchoring element and connecting element can be provided after insertion of the anchoring element so that the anchoring element itself, for example, a bone screw need no longer be turned in the bone, which can lead to an undesired loosening of a screw once screwed in.

In contrast to bone screws which have a forked head for accommodating a connecting element, the provision of a connection between the anchoring element and the connecting element in the case of known fixation devices has proven to be extremely complicated since, on the one hand, the fixation device must be secured to the anchoring element and, on the other hand, the connecting element must be secured to the fixation device.

It is, therefore, the object of the present invention to improve an orthopedic fixation device as well as an orthopedic fixation system of the respective type described at the outset such that the connecting element can be secured on the anchoring element in a particularly simple manner.

SUMMARY OF THE INVENTION

This object is accomplished in accordance with the invention, in an orthopedic fixation device of the type described at the outset, in that a single tensioning member supported so as to be movable is provided for transferring the fixation device from the adjusting position into the fixing position and vice versa.

In contrast to the fixation devices known from the state of the art, it is sufficient to move only the tensioning member, whereby the fixation device can be secured, on the one hand, on the connecting element and, on the other hand, on the anchoring element. Therefore, only one locking step is necessary in order to secure three elements relative to one another at the same time. This is advantageous, in particular, when the connecting element is intended to be secured to the anchoring element laterally offset relative to a longitudinal axis of this anchoring element. In any case, the fixation device according to the invention allows the anchoring element to be inserted first of all into a bone or a bone fragment in the desired manner, the connecting element to subsequently be adjusted relative to the anchoring element in the desired manner and the fixation device to then be secured not only to the anchoring element but also to the connecting element in a single step as a result of movement of the tensioning member.

It is advantageous when the fixation device comprises at least one first supporting element and when the tensioning member is supported on the at least one first supporting element so as to be rotatable. The fixation device can then be transferred from the adjusting position into the fixing position as a result of a simple rotation of the tensioning member relative to the first supporting element.

It is favorable when the fixation device comprises at least one first supporting element and when the tensioning member is supported relative to the first supporting element so as to be translatable. This configuration, also in combination with a possible rotatability of the tensioning member relative to the first supporting element, allows transfer of the fixation device from the adjusting position into the fixing position as a result of a simple, translational movement of the tensioning member relative to the first supporting element.

In accordance with a preferred embodiment of the invention, it may be provided for the connecting element, in the adjusting position, to be displaceable relative to the anchoring element parallel to itself towards the anchoring element or away from it. This configuration makes it possible, for example, to hold the connecting element on the anchoring element in the adjusting position by means of the fixation device and, when required, to reduce a distance between the connecting element and the connecting section of the anchoring element in the desired manner without the connecting element needing to be pivoted relative to the anchoring element.

In order to ensure a particularly good securement of the connecting element on the fixation device in the fixing position, it is advantageous when the fixation device has a connecting element receiving means, which corresponds to the connecting element, for accommodating the connecting element.

In a similar way, an optimum securement of the fixation device on the connecting section of the anchoring element can be ensured when the fixation device has a connecting section receiving means, which corresponds to the connecting section, for accommodating the connecting section.

In order to facilitate pivoting of the connecting element relative to the anchoring element, it is advantageous when the connecting section receiving means is rotatable about a first axis of rotation relative to the connecting element receiving means.

In principle, it would be conceivable to secure the anchoring element, the fixation device and the connecting element in the fixing position by means of form locking connections. In accordance with a preferred embodiment of the invention, it may be provided for a first clamping device to be provided for clampingly securing the fixation device on the connecting element in the fixing position, for a second clamping device to be provided for clampingly securing the fixation device on the anchoring element in the fixing position and for the first clamping device to comprise the tensioning member and for the second clamping device to comprise the tensioning member. The tensioning member is, in the configuration according to the invention, therefore part of both clamping devices which makes it possible to actuate both clamping devices, i.e., transfer the fixation device into the fixing position or to release them, i.e., transfer the fixation device from the fixing position into the adjusting position at the same time as a result of movement of the tensioning member.

It is advantageous when the fixation device comprises a first supporting element supporting the connecting element receiving means and a second supporting element which supports the connecting section receiving means and is supported on the first supporting element so as to be rotatable about an axis of rotation in the adjusting position. The two supporting elements form, as it were, a two-part movable frame and enable the connecting element to be pivoted relative to the anchoring element about the first axis of rotation.

The construction of the fixation device is particularly simple when the tensioning member forms a bearing shaft defining the first axis of rotation. The tensioning member therefore has a double function; on the one hand, it serves as a bearing shaft, on the other hand, as a means for transferring the fixation device from the adjusting position into the fixing position and vice versa. The design of the fixation device may also be simplified as a result of this construction.

It is advantageous when the first clamping device comprises a first clamping element which has a slide-on surface which abuts directly or indirectly on a first actuating surface of a first clamping member of the first supporting element and when the first clamping element is movable as a result of movement of the tensioning member in such a manner that the first slide-on surface slides on the first actuating surface and can reduce a cross section of the connecting element receiving means in such a manner that the connecting element can be secured in the connecting element receiving means. It is, therefore, possible to move the tensioning member and as a result of its movement drive, so to speak, the first clamping element which can move a clamping member directly or indirectly as a result of the slide-on surface sliding on the actuating surface. As a result, the fixation device is transferred from the adjusting position into the fixing position in that the cross section of the connecting element receiving means is reduced by the slide-on movement which leads to a desired clamping of the connecting element in the connecting element receiving means.

In order to be able to use individual parts of the fixation device for different sizes of supporting elements, it is favorable when a first force transfer member arranged between the first slide-on surface and the first actuating surface is provided for transferring a force from the first clamping element to the first clamping member. For example, the parts could also be manufactured from different materials.

It is advantageous when the first slide-on surface and the first actuating surface are inclined relative to the first axis of rotation. As a result, a slide-on movement can take place when the tensioning member is moved parallel to the axis of rotation. A parallel movement also results indirectly due to rotation of the tensioning member when this is designed, for example, in the form of a screw bolt which therefore facilitates a superimposed translation-rotation movement.

In accordance with a further, preferred embodiment of the invention, it may be provided for the first slide-on surface to be a first outer surface of a first eccentric rotatable about the first axis of rotation and for the first actuating surface to be curved concavely in the direction towards the first axis of rotation at least in sections. As a result of the eccentric, a distance between the first outer surface and the first actuating surface can be altered as a result of a rotation of the tensioning member and clamping brought about in this way. The actuating surface can be shaped, for example, so as to be hollow cylindrical in sections, the outer surface of the eccentric so as to be cylindrical.

The first clamping element can be advantageously designed in the shape of a cone. The cone can, therefore, have a conical outer surface which serves at the same time as a slide-on surface. A slide-on movement relative to the first actuating surface can be brought about with the cone in every rotary position of the tensioning member, for example, as a result of a translational movement of the cone parallel to the first axis of rotation.

Assembly of the fixation device is simplified when the first clamping element and the tensioning member are designed in one piece. In this way, it is possible to prevent the clamping element and the tensioning member from being able to detach from one another in an undesired manner.

Depending on the construction of the fixation device, it may, however, be advantageous with a view to the assembly when the first clamping element and the tensioning member are designed in two parts. This allows, for example, parts to be pushed together first of all and then securely connected to one another.

The first clamping element and the tensioning member are preferably connected to one another so as to be non-rotatable. This prevents any loosening of the first clamping element from the tensioning member as a result of rotation of the tensioning member.

It may favorably be provided for the tensioning member to have a first external thread section, for the first clamping element to have a first internal thread section corresponding to the first external thread section and for the first clamping element to be displaceable parallel to itself as a result of rotation of the tensioning member about its longitudinal axis. This construction is similar to the construction of a threaded spindle, wherein the tensioning member is used as a drive element in order to be able to displace the clamping element parallel to itself. The clamping element is advantageously guided for this purpose in a corresponding guide which prevents any rotation of the clamping element as a result of a rotary movement of the tensioning member.

Furthermore, it may be favorable when the second clamping device comprises a second clamping element which has a second slide-on surface which abuts directly or indirectly on a second actuating surface of the second supporting element and when the second clamping element can be moved as a result of movement of the tensioning member in such a manner that the second slide-on surface slides on the second actuating surface and a clamping member limiting the connecting section receiving means in sections can be moved in such a manner that a cross section of the connecting section receiving means can be reduced such that the connecting section of the anchoring element can be secured in the connecting section receiving means. The second clamping element can be moved with the tensioning member, whereby a slide-on movement between the clamping element and the clamping member abutting directly or indirectly on it is made possible in order to reduce a cross section of the connecting section receiving means. As a result of the reduction in the cross section, the connecting section can be secured in the connecting section receiving means.

A slide-on movement is possible in a simple manner when the second slide-on surface and the second actuating surface are inclined relative to the first axis of rotation. Slide-on movement is thus made possible when the tensioning member is moved, for example, as a result of movement parallel to the first axis of rotation either as a result of a pure translation movement or as a result of a superimposed translation-rotation movement.

It Is favorable when the second slide-on surface Is a second outer surface of a second eccentric rotatable about the first axis of rotation and when the second actuating surface is curved concavely in the direction towards the first axis of rotation at least in sections. The eccentric, the outer surface of which is arranged eccentrically to the first axis of rotation, can reduce a distance between the second slide-on surface and the second actuating surface when the tensioning member and, with it, the eccentric is rotated about the first axis of rotation. The second outer surface may be a cylindrical surface, the second actuating surface a hollow cylindrical surface or at least a surface section of this type.

A particularly simple construction of the fixation device results when the second clamping element is designed at least partially in the shape of a cone. This also means that only a part or a section of the second clamping element may have a conical or at least inclined surface. Such a clamping element is particularly easy to produce.

In order to increase the stability of the fixation device, it may be advantageous when the second clamping element and the tensioning member are designed in one piece. Furthermore, this avoids the second clamping element and the tensioning member being able to become detached from one another when this is not desired.

The second clamping element and the tensioning member are preferably designed in two parts. This can make an assembly of different parts even possible at all. Furthermore, the combination of different tensioning members with different clamping elements is possible during the assembly.

In order to ensure that the second clamping element is rotated as well as a result of rotation of the tensioning member, it is favorable when the second clamping element and the tensioning member are connected to one another so as to be non-rotatable.

In accordance with a preferred embodiment of the invention, it may be provided for the tensioning member to have a second external thread section, for the second clamping element to have a second internal thread section corresponding to the second external thread section and for the second clamping element to be displaceable parallel to itself as a result of rotation of the tensioning member about its longitudinal axis. As a result of this configuration, a spindle drive is, as it were, formed for driving the second clamping element as a result of rotation of the tensioning member. So that the second clamping element is not co-rotated as a result of rotation of the tensioning member, a corresponding guide for the second clamping element can be provided.

The first and the second external thread sections are favorably thread sections running in opposite directions. This makes it possible for the two clamping elements to be moved at the same time towards one another or away from one another as a result of rotation of the tensioning member.

In this respect, it may be advantageous when the first external thread section is a right-hand thread section and when the second external thread section is a left-hand thread section. This makes it possible, for example, to drive the two clamping members with the tensioning member, as a result of rotation of the tensioning member in the clockwise direction, in such a manner that they are moved towards one another, whereby the fixation device can be transferred from the adjusting position into the fixing position.

It is advantageous when the second supporting element is supported on the connecting section via the second clamping member in the fixing position. In this way, connecting sections with different cross sections can be accommodated by the connecting section receiving means and can be secured in it.

So that as few individual parts as possible have to be joined together during the production of the fixation device, it is advantageous when the second clamping member and the second supporting element are designed in one piece. For example, the second clamping member can be designed in the form of a movable tab held on the supporting element.

In order to be able to adapt the fixation device, when required, to specific anchoring elements during a surgical procedure, it is favorable when the second clamping member and the second supporting element are designed in two parts. This allows clamping members of a desired strength or thickness to be selected and arranged on the fixation device.

So that the connecting element can be moved parallel to itself in the direction towards the anchoring element, it is advantageous when the second supporting element is supported on the connecting section so as to be rotatable about a second axis of rotation in the adjusting position. In other words, this means that the connecting section itself or the second supporting element each form a supporting element for the respectively other element for forming a rotary bearing.

A particularly simple construction of the fixation device results when the first and the second axes of rotation extend parallel to one another. In addition, movement of the connecting element parallel to itself towards the anchoring element is allowed in this way.

In order to be able to adjust an angle of inclination of the connecting element relative to the anchoring element, it is advantageous when the connecting element receiving means is supported on the first supporting element so as to be rotatable about a third axis of rotation and when the third axis of rotation extends transversely to a longitudinal axis of the connecting element receiving means. The rotatability can, in addition, be limited by angular stops provided accordingly so that a rotatability, for example, in an angular range of ±30° is possible, preferably ±15°.

An optimum adaptation for connecting different bone parts or bone fragments may be achieved when the third axis of rotation extends transversely to the first and/or to the second axis of rotation.

So that the fixation device can be secured on the anchoring element only after anchoring of the anchoring element in or on a bone, it is favorable when the connecting section forms the proximal end of the anchoring element or is arranged in the area of the proximal end of the anchoring element. It is, therefore, possible to place the fixation device, for example, onto the connecting section after insertion of the anchoring element.

In principle, it would be conceivable to design the connecting section receiving means in such a manner that a cylindrical connecting section can be accommodated. In order to increase the adjustability of the fixation device and, therefore, of the connecting element relative to the anchoring element even further, it is advantageous when the connecting section receiving means Is designed in the form of a spherical joint receiving means for accommodating a spherical connecting section.

So that the tensioning member can be moved in a simple manner, it is advantageous when it has a tool receiving means for accommodating a tensioning tool and when the tensioning member is movable with the tensioning tool.

The object specified at the outset is accomplished in accordance with the invention, in addition, in an orthopedic fixation system of the type described at the outset, in that the at least one orthopedic fixation device is one of the fixation devices described above. As already explained, the fixation device can be transferred from the adjusting position into the fixing position in a single step with such a fixation device. Dependent on the special configuration of the fixation device, the overall orthopedic fixation system then has the advantages described above.

In order to be able to connect the fixation device to the anchoring element in a simple manner, it is advantageous when the connecting section is designed so as to be thread-free and is cylindrical or essentially cylindrical in shape. In the adjusting position, the fixation device can be rotated in a simple manner relative to the anchoring element since the connecting section forms a more or less perfect bearing shaft.

In order to be able to form a spherical joint with the fixation device, it is favorable when the connecting section of the anchoring element is in the shape of a spherical cap or essentially in the shape of a spherical cap.

In accordance with a preferred embodiment of the fixation system, it may be provided for the anchoring element to comprise a screw thread section forming its distal end for screwing into a bone.

Furthermore, it can be advantageous when the anchoring element comprises a hook forming its distal end for anchoring the anchoring element in a bone.

The connecting element is preferably a bar or a connecting plate with at least one bar-like plate section. Connecting elements of this type may be connected in a simple manner by means of a fixation device according to the invention to an anchoring element of any optional type.

The following description of preferred embodiments of the invention serves to explain the invention in greater detail in conjunction with the drawings.

BRIEF DESCRIPTION OF THE DRAWINGS

FIG. 6: shows a sectional view similar to FIG. 5 through a second embodiment of a fixation device in the adjusting position;
FIG. 7: shows a view similar to FIG. 6 of the second embodiment but in the fixing position.

DETAILED DESCRIPTION OF THE INVENTION

Figure 1:
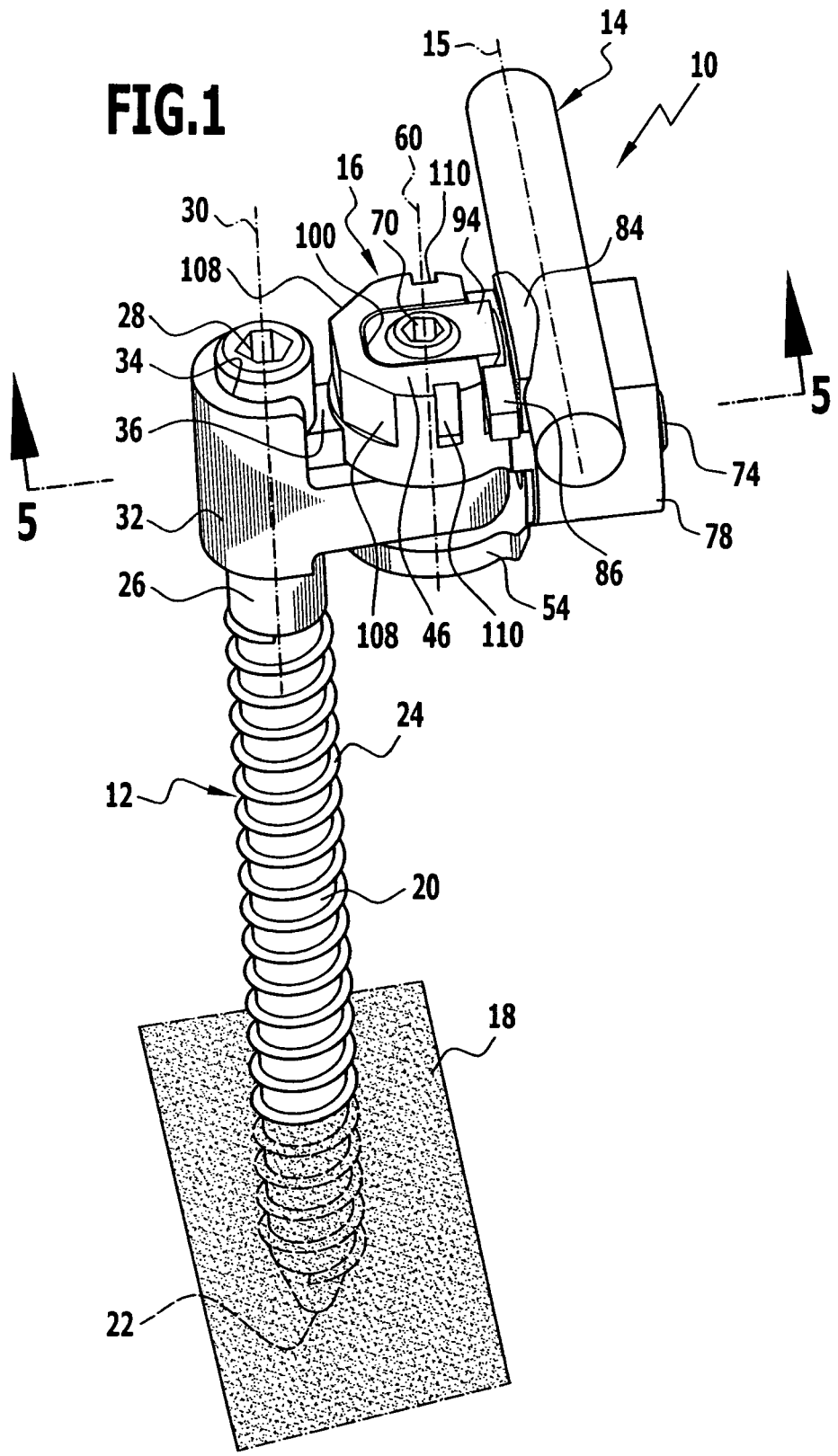
FIG. 1: shows a perspective overall view of a first embodiment of a fixation system according to the invention.
Figure 2:
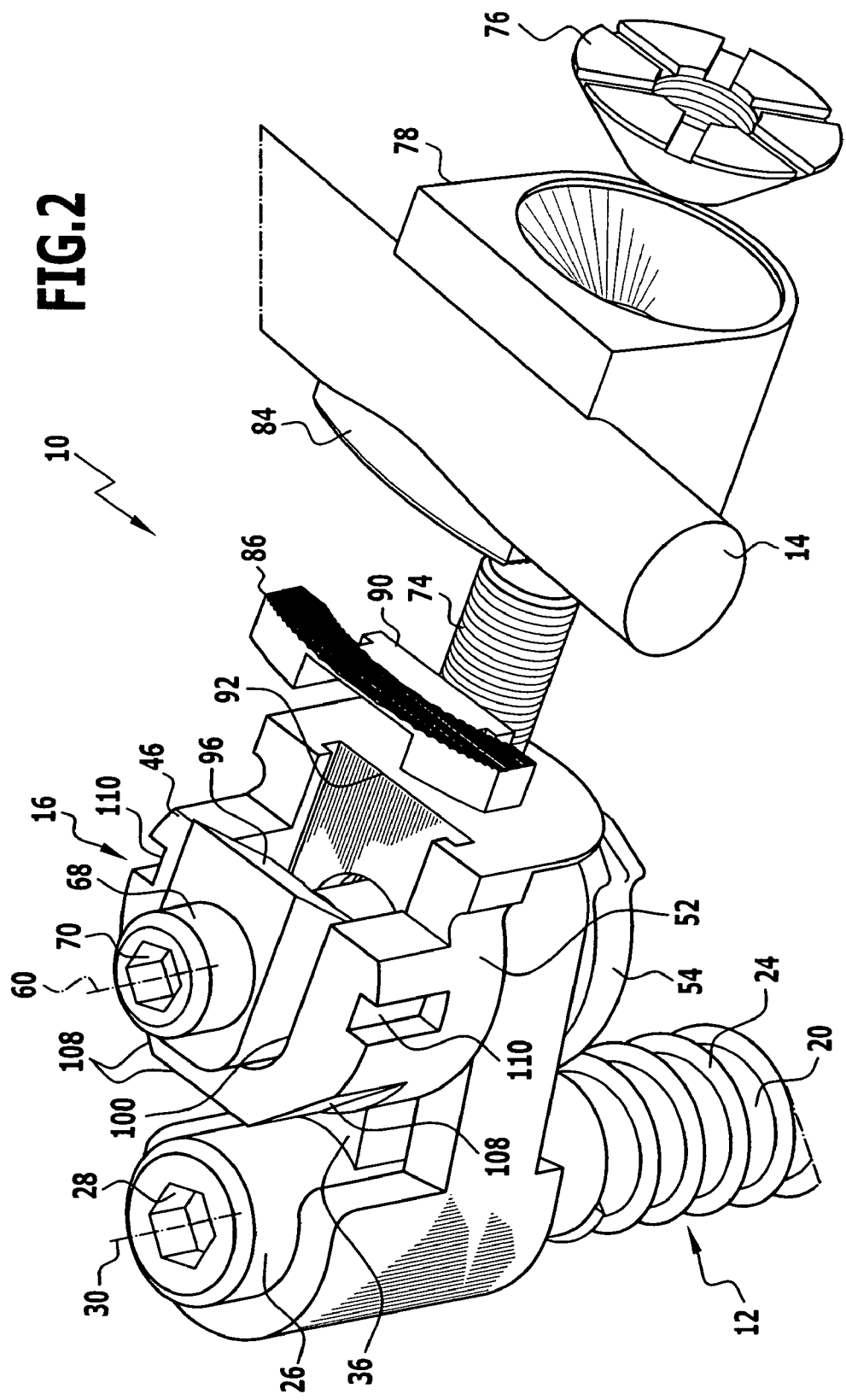
FIG. 2: shows a partially disassembled fixation device in the fixing position.
Figure 3:
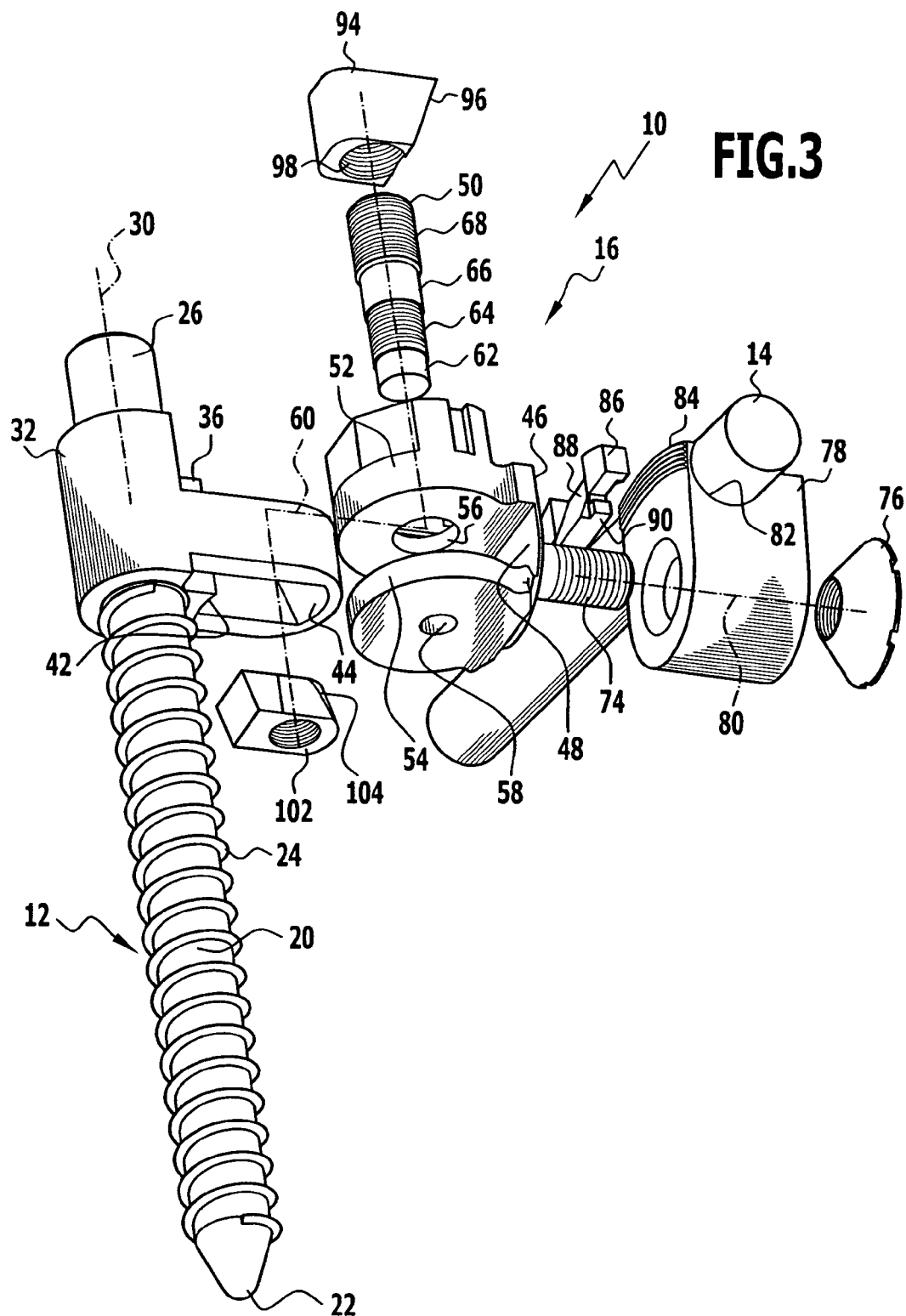
FIG. 3: shows an exploded illustration of the fixation system illustrated in FIG. 1.
Figure 4:
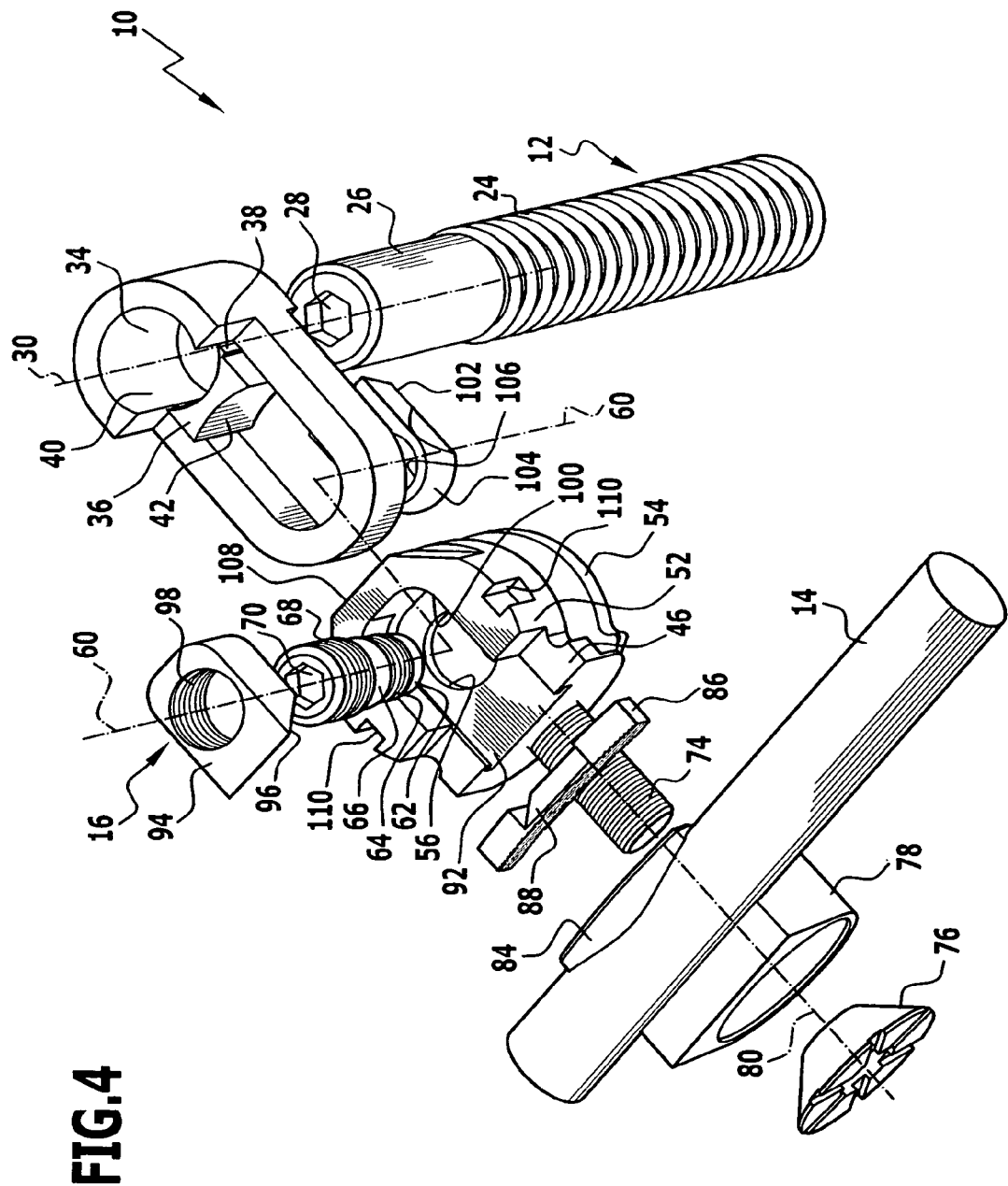
FIG. 4: shows a further, perspective view of the exploded illustration in FIG. 3.

FIGS. 1 to 5 illustrate by way of example part of a fixation system provided altogether with the reference numeral 10 with an anchoring element in the form of a bone screw 12, a connecting element in the form of a bar 14 defining a longitudinal axis 15 as well as a first embodiment of a clamping connector 16 according to the invention, with which the bar 14 can be secured to the bone screw 12 in a fixing position.

Different bones or bone fragments 18 may be positioned and fixed relative to one another with the fixation system in that the same or similar bone screws 12 are turned into the respective bone fragment 18 and connected to one another by means of the bar 14, in particular, by using the clamping connector 16 or similar connecting elements. In principle, the bar 14 could also be secured to the second bone fragment which is not illustrated via a bone screw with a completely different configuration and having a clamping part arranged thereon.

The bone screw 12 has an elongated cylindrical shaft 20 which is provided with an external thread 24 over approximately three quarters of its overall length proceeding from a tip 22 for screwing into the bone fragment 18. A proximal end of the bone screw 12 forms a cylindrical connecting section 26 which has a smooth outer cylindrical surface. For turning the bone screw 12 into the bone fragment 18, a tool element receiving means in the form of an internal polygon 28 is provided which is designed so as to be symmetric to a longitudinal axis of the bone screw 12.

The bar 14 has a suitable length for connecting two anchoring elements to one another and has a circular cross section.

The clamping connector 16 comprises an offset bridge 32 which has an essentially hollow cylindrical connecting section receiving means 34 which can be pushed onto the connecting section 26 parallel to the longitudinal axis 30 in a distal direction of the bone screw. The offset bridge 32 is, altogether, designed essentially in the shape of an oval sleeve which has its greatest height in the area of the connecting section receiving means 34. In the assembled state, the connecting section 26 is surrounded over approximately 220° of its circumference by a first, curved wall section of the oral sleeve, the height of which, apart from the first curved wall section, is in the remaining area only approximately half the overall height in the area of the connecting section receiving means 34.

A clamping member 36 pointing towards the longitudinal axis 30 abuts on the connecting section 26 in the direction towards the section of the offset bridge 32 which is lower in height and this clamping member is connected in a spring-like manner to the part of the offset bridge 32 limiting the connecting section receiving means 34 via a narrow web 38 extending parallel to the longitudinal axis 30. The clamping member 36 is essentially designed in a parallelepiped shape and has a concave contact surface 40 which points in the direction towards the connecting section 26 and a pressure surface 42 which points in the opposite direction. The clamping member 36 extends parallel to the longitudinal axis over a length which is greater than a height of the lower section of the offset bridge 32 so that the clamping member 36 projects somewhat beyond a wall of the offset bridge 32 on both sides. Furthermore, an inner surface of the oval offset bridge 32 is inclined through approximately 15° relative to the longitudinal axis 30, namely in a distal direction away from the longitudinal axis 30, in a second curved sector which points towards the connecting section receiving means 34. The inclined surface forms a conical actuating surface section 44.

The area of the offset bridge 32 pointing away from the connecting section receiving means 34 is inserted into a U-shaped receiving means 48 of a joint member 46 and secured by means of a tensioning member 50. For this purpose, an upper side wall 52 and a lower side wall 54, which limit the receiving means 48 to the side, are provided with concentric bores 56 and 58, wherein the bore 58 provided in the lower side wall 54 is smaller in diameter than the bore 56 in the upper side wall 52. The tensioning member 50 defines with its longitudinal axis 60 a first axis of rotation, about which the joint member 46 can be pivoted relative to the offset bridge 32.

The tensioning member 50 is divided altogether into four sections, namely a first, cylindrical bearing section 62 corresponding to the bore 58 and a right-hand thread section 64 which adjoins thereto and is somewhat larger in its external diameter than the bearing section 62. The right-hand thread section 64 is adjoined by a second cylindrical section 66 which corresponds to the bore 56 and the external diameter of which is somewhat larger than that of the right-hand thread section 64. An end of the tensioning member 50 located opposite the bearing section 62 is formed by a left-hand thread section 68 which has an external diameter which is somewhat enlarged in comparison with the cylindrical section 66. As a result of this configuration, the tensioning member 50 can be pushed through the bore 56 starting with the bearing section 62, wherein following the assembly of the clamping connector 16 the bearing section 62 and the cylindrical section 66 are each guided in the bores 56 and 58, respectively. A tool element receiving means in the form of an inner polygon 70 is provided concentrically to the longitudinal axis 60 in the area of the left-hand thread section 68 for accommodating a tensioning tool 72, the distal end of which is illustrated schematically in FIG. 5. The tensioning member 50 can be turned about its longitudinal axis 60 with the tensioning tool 72.

A threaded bolt 74, on which a clamping jaw 78 is secured by means of a nut 76, projects from the joint member 46 transversely to the longitudinal axis and pointing in the opposite direction to the receiving means 48. A longitudinal axis 80 of the threaded bolt 74 extends transversely to the longitudinal axis 60. A connecting element receiving means is provided on the clamping jaw 78 in the form of an essentially hollow cylindrical bar receiving means 82, into which the bar 14 can be pushed or also clicked transversely to its longitudinal axis. For this purpose, the bar receiving means 82 is open parallel to its longitudinal axis 15 over a sufficient angular range. The bar receiving means 82 has a clamping section 84 which points in the direction towards the longitudinal axis 60 and can be somewhat springy as a result of a material weakening. A clamping member 86 abuts on the clamping section 84 and this has a plane actuating surface 88 inclined through approximately 25° relative to the longitudinal axis 60. The clamping member 86 is supported on the joint member 46 for displacement parallel to the longitudinal axis 80, namely in that a T-shaped projection 90 of the clamping member 86 is guided in a T-shaped groove 92 in the upper side wall 52.

A first clamping member 94, which is designed essentially in a parallelepiped shape, is provided for clampingly tensioning the bar 14 in the bar receiving means 82, wherein an end face corresponding to the actuating surface 88 is beveled and forms a slide-on surface 96. The first clamping member 94 is provided with a bore having an internal thread 98 corresponding to the left-hand thread section 68 and is guided in a U-shaped recess 100 on an upper side of the upper side wall 52 and, as a result, is secured against any rotation about the longitudinal axis 60.

Furthermore, a second clamping member 102 is provided which is designed in the shape of a parallelepiped and has a second slide-on surface 104 corresponding to the conical actuating surface section 44. Furthermore, the second clamping member 102 is provided with a bore provided with an internal thread 106, wherein the internal thread 106 is designed to correspond to the right-hand thread section 64.

In addition, flattened areas 108 inclined relative to one another at a respective angle of 45° are provided on an outer wall of the U-shaped recess 100 as well as two recesses 110 located diametrically opposite one another. The flattened areas 108 and the recesses 110 serve to accommodate an insert tool for the clamping connector 16 which is not illustrated.

The mode of operation of the fixation system 10, in particular, the clamping connector 16 will be explained in greater detail in the following with reference to FIG. 5.

Figure 5:
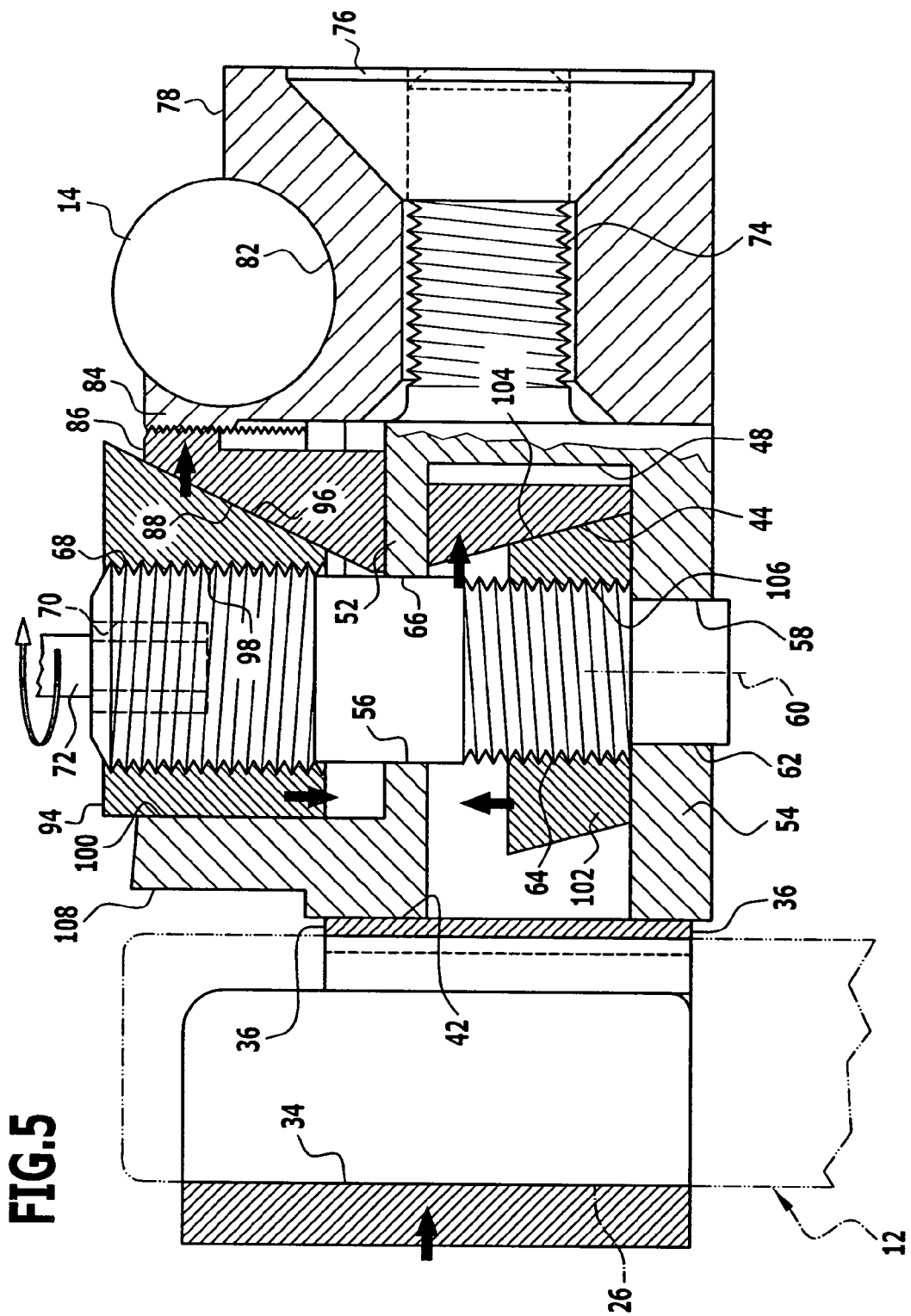
FIG. 5: shows a sectional view along line 5-5 in FIG. 1.

The clamping connector 16 is illustrated in FIG. 5 in the so-called adjusting position. This means that the connecting section 26 can be inserted into the connecting section receiving means 34 which allows a rotation of the offset bridge 32 about the longitudinal axis 30 at the same time. Furthermore, the joint member 46 can be pivoted about the longitudinal axis 60 relative to the offset bridge 32. In addition, the bar 14 can be displaced in the bar receiving means 82.

Once the bone screw 12 has been anchored in the bone fragment 18 in the desired manner, the clamping connector 16 is placed on the bone screw 12 and the bar 14 positioned in the bar receiving means 82. A surgeon can now adjust a relative position of the bar 14 in relation to the bone screw 12 in the desired manner. In this respect, he also has the possibility of varying an inclination of the longitudinal axis 15 of the bar 14 relative to the longitudinal axes 30 and 60, namely by pivoting the clamping jaw 78 about the longitudinal axis 80. In this respect, lateral stops are provided which are not illustrated in detail and which limit a pivoting range of the clamping jaw 78 about the longitudinal axis 80 to approximately ±15°.

In order to secure the bar 14 on the bone screw 12, the tensioning member 52 is turned in the clockwise direction by means of the tensioning tool 72. As a consequence, the first clamping member 94 is moved in the direction towards the upper side wall 52 and the second clamping member 102 is likewise moved in the direction towards the upper side wall 52. Altogether, the two clamping members 94 and 102 are, therefore, moved towards one another during rotation of the tensioning member in the clockwise direction. As a result of the movement of the first clamping member 94 parallel to the longitudinal axis 60, the first slide-on surface 96 slides on the actuating surface 88, whereby the clamping member 86 is moved in the direction towards the bar 14 which is indicated by an arrow and presses the clamping section 84 in the direction towards the bar 14. As a result, the bar 14 is clampingly secured in the bar receiving means 82. The second slide-on surface 104 slides in an analogue manner on the conical actuating surface section 44, with the result that the entire offset bridge 32 is drawn in the direction of the arrow to the left in FIG. 5 parallel to the longitudinal axis 80. The pressure surface 42 abuts on rounded end faces of the joint member 46 such that the clamping member 36 is moved relative to the connecting section 26 towards it, whereby a cross section of the connecting section receiving means 34 is reduced altogether and the connecting section 26 is held in a clamping manner.

It is possible with the clamping connector 16 according to the invention to pivot the bar 14 about two axes of rotation extending parallel to one another, namely the longitudinal axes 30 and 60, relative to the connecting section 26. In this way, a displacement of the bar 14 parallel to itself in the direction towards the connecting section 26 is possible. Furthermore, it is possible solely as a result of movement of the tensioning member 50 to cause the clamping connector 16 to be transferred from an adjusting position, in which not only the bar 14 but also the connecting section 26 are held loosely on the clamping connector 16, into the fixing position, in which not only the bar 14 but also the connecting section 26 are secured on the clamping connector 16 so as to be immovable. In order to fix the bar 14 to the bone screw 12, only one locking step is, therefore, necessary which is carried out by way of rotation of the tensioning member 50.

In the reverse way, the clamping connector 16 may also be transferred again from the fixing position into the adjusting position.

In the following, seven further or also alternative embodiments of the clamping connector 16 will be described in greater detail in conjunction with FIGS. 6 to 13. For the sake of simplicity, identical or very similar parts in comparison with the clamping connector 16 are given the same reference numerals. Modified parts or elements of the clamping connector are explicitly described and given their own reference numerals.

A second embodiment of a clamping connector provided altogether with the reference numeral 120 is illustrated in FIGS. 6 and 7. A tensioning member provided, altogether, with the reference numeral 122 differs from the tensioning member 50 due to the fact that instead of the two thread sections 64 and 68 adjacent to the bearing section 62 and the cylindrical section 66, respectively, a respective cylindrical section 124 and 126, respectively, is provided, arranged eccentrically in relation to the longitudinal axis 60. In addition, in comparison with the clamping connector 16, a hollow cylindrical section 128 is provided instead of the conical actuating surface section 44 and an outer surface of the cylindrical section 124 slides on this hollow cylindrical section as a result of rotation of the tensioning member 122 and can move the offset bridge 130 provided altogether with the reference numeral 130 in the direction towards the bar 14. The clamping member 86 with its actuating surface 88a can be displaced in an analogous way by means of the cylindrical section 126 in the direction towards the clamping section 84, whereby the bar 14 can be held in a clamping manner in the bar receiving means 82. Therefore, interacting actuating and slide-on surfaces are also provided in the case of the clamping connector 120, wherein these are not inclined relative to the longitudinal axis 60. Slide-on movement is brought about on account of the eccentricity of the cylindrical sections 124 and 126, wherein this eccentricity is apparent on the basis of an eccentric axis 132 which is drawn in parallel to the longitudinal axis 60 in FIGS. 6 and 7 and forms an axis of symmetry of the cylindrical sections 124 and 126.

Figure 8:
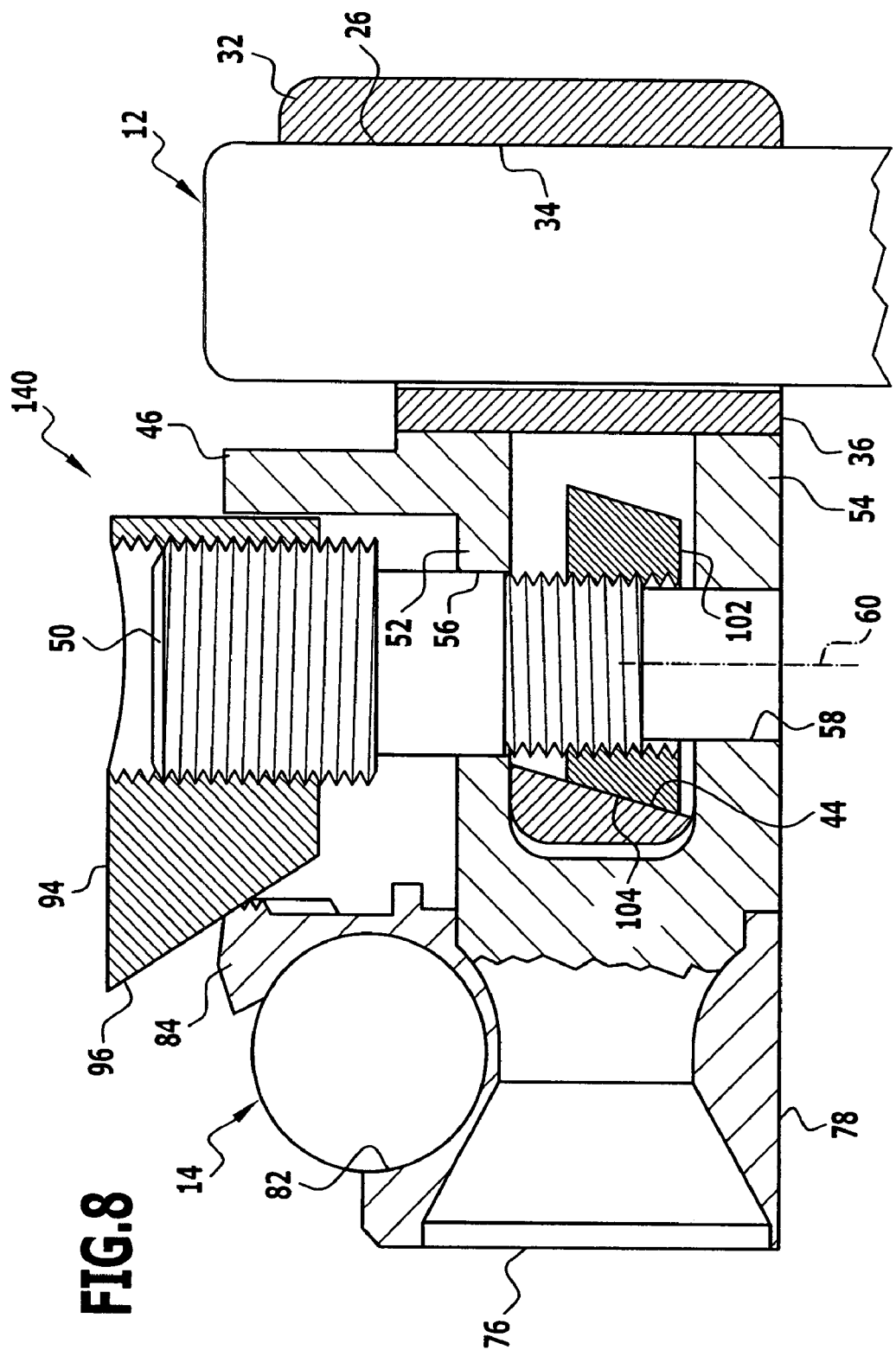
FIG. 8: shows a sectional view similar to FIG. 5 through a third embodiment of a fixation device.

A third embodiment of a clamping connector provided altogether with the reference numeral 140 is illustrated in FIG. 8. The clamping connector 140 corresponds almost identically to the clamping connector 16 but the clamping member 86 has been omitted in this case and so the first slide-on surface 96 abuts directly on the clamping section 84 of the bar receiving means 82. The first clamping member 94 therefore extends somewhat further in the direction towards the bar receiving means 82 than in the case of the clamping connector 16. Otherwise, the mode of operation of the clamping connector 140 corresponds to the mode of operation described in conjunction with the clamping connector 16.

Figure 9:
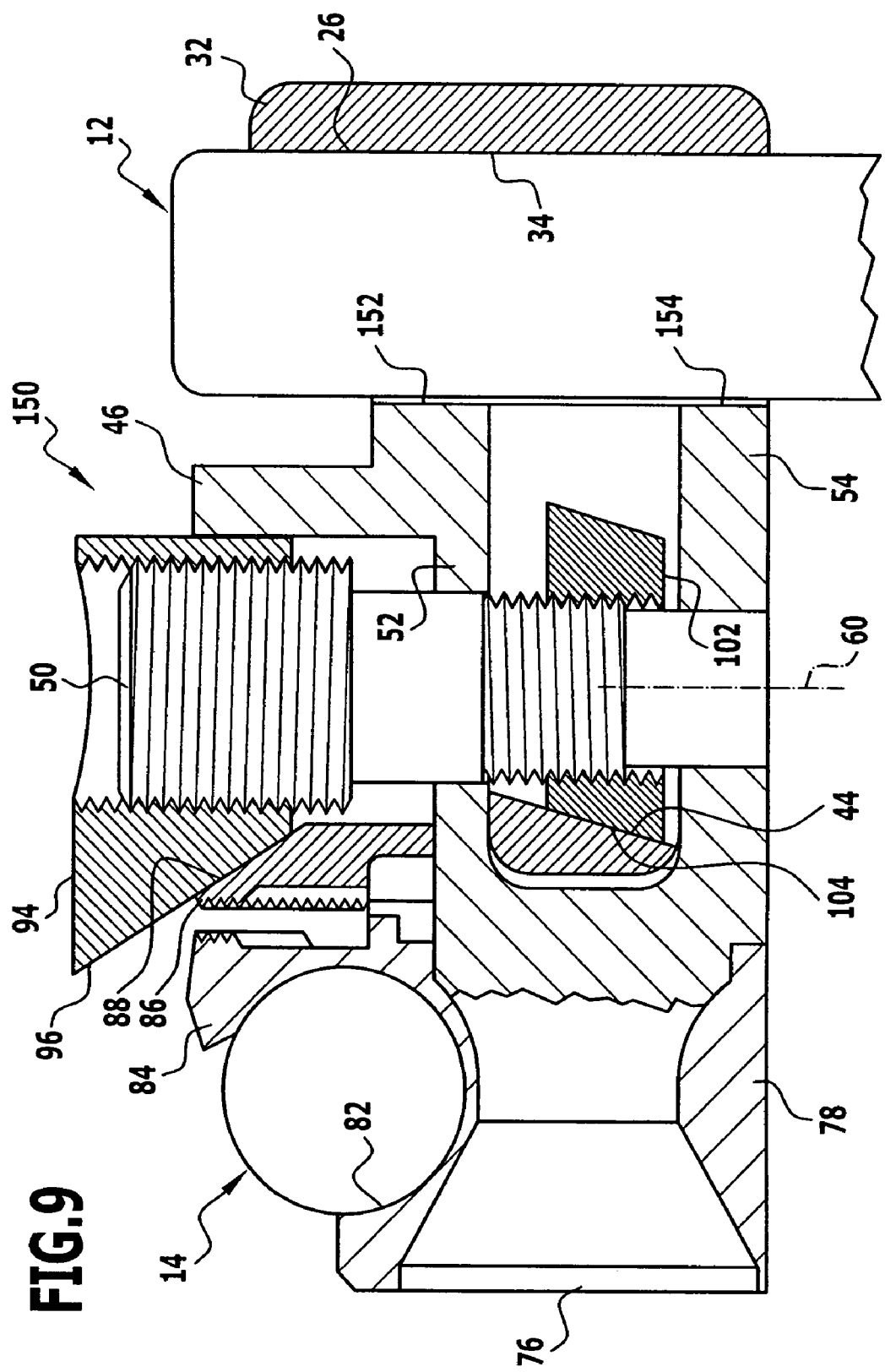
FIG. 9: shows a sectional view similar to FIG. 5 through a fourth embodiment of a fixation device.

A fourth embodiment of a clamping connector is provided in FIG. 9 altogether with the reference numeral 150. It differs from the clamping connector 16 only due to the fact that the clamping member 36 has been omitted. End faces 152 and 154 of the upper side wall 52 and the lower side wall 54, respectively, are shaped concavely for this purpose and abut directly on the connecting section 26 of the bone screw 12. The connecting section 26 is held in a clamping manner in the fixing position between the end faces 152 and 154, respectively, on the one hand, and an inner surface of the connecting section receiving means 34 located diametrically opposite, on the other hand. As for the rest, the mode of operation of the clamping connector 150 corresponds to that already explained in greater detail in conjunction with the clamping connector 16.

Figure 10:
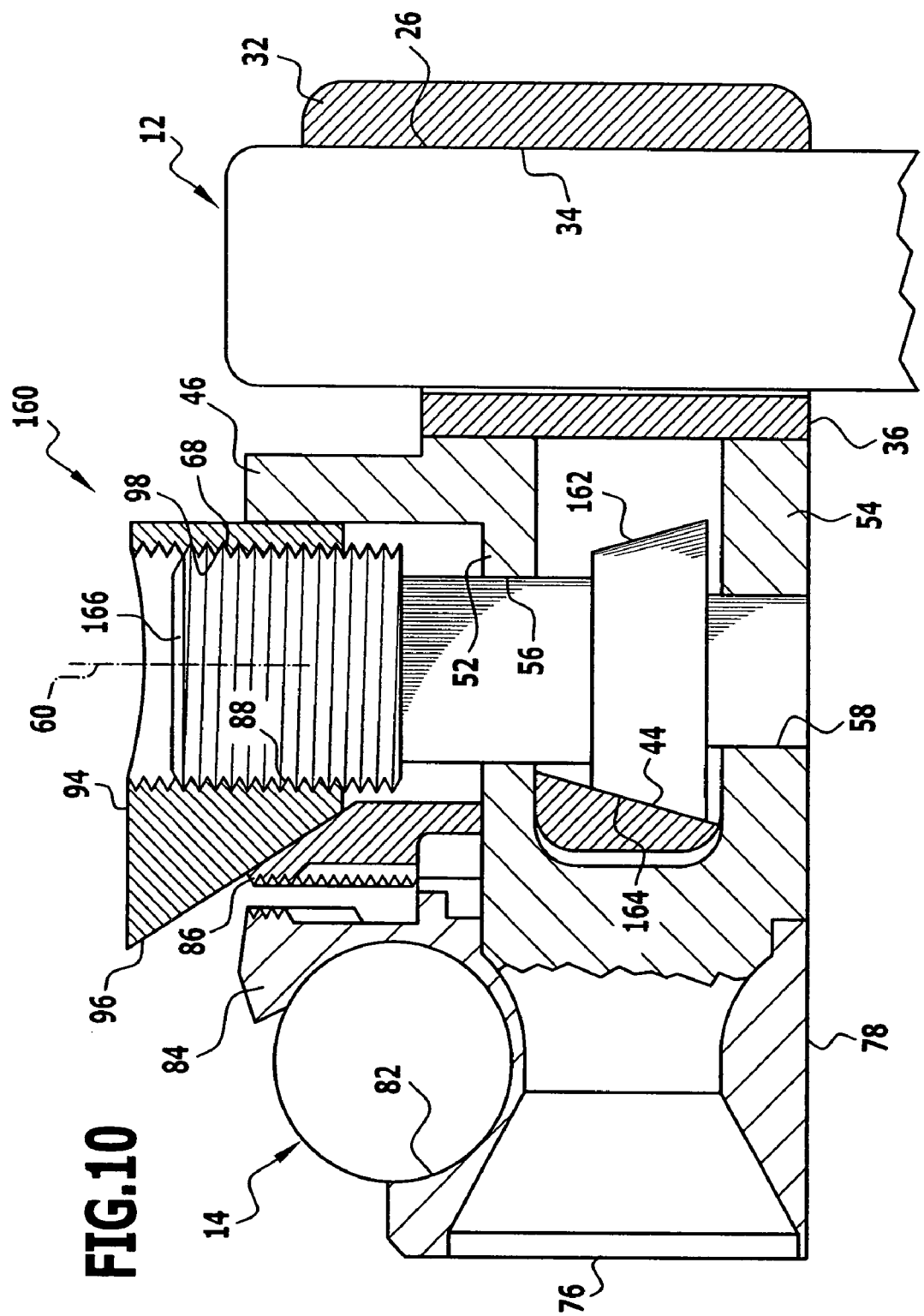
FIG. 10: shows a sectional view similar to FIG. 5 through a fifth embodiment of a fixation device.

A clamping connector provided altogether with the reference numeral 160 is illustrated in FIG. 10 and this differs from the clamping connector 16 due to the fact that instead of the second clamping member 102 a cone 162 is provided, the inclined conical outer surface 164 of which has a function corresponding to the second slide-on surface 104. The cone 162 is secured on the tensioning member provided with the reference numeral 166 so as to be axially non-movable. As a result of rotation of the tensioning member 166 in the clockwise direction about the longitudinal axis 60, the first clamping member 94 is drawn in the direction towards the cone 162, whereby the offset bridge 32 is drawn in the direction towards the bar 14 and, as a result, tensioned in a clamping manner in the connecting section receiving means 34, the bar 14 in the bar receiving means 82 due to the exertion of pressure on the clamping section 84.

Figure 11:
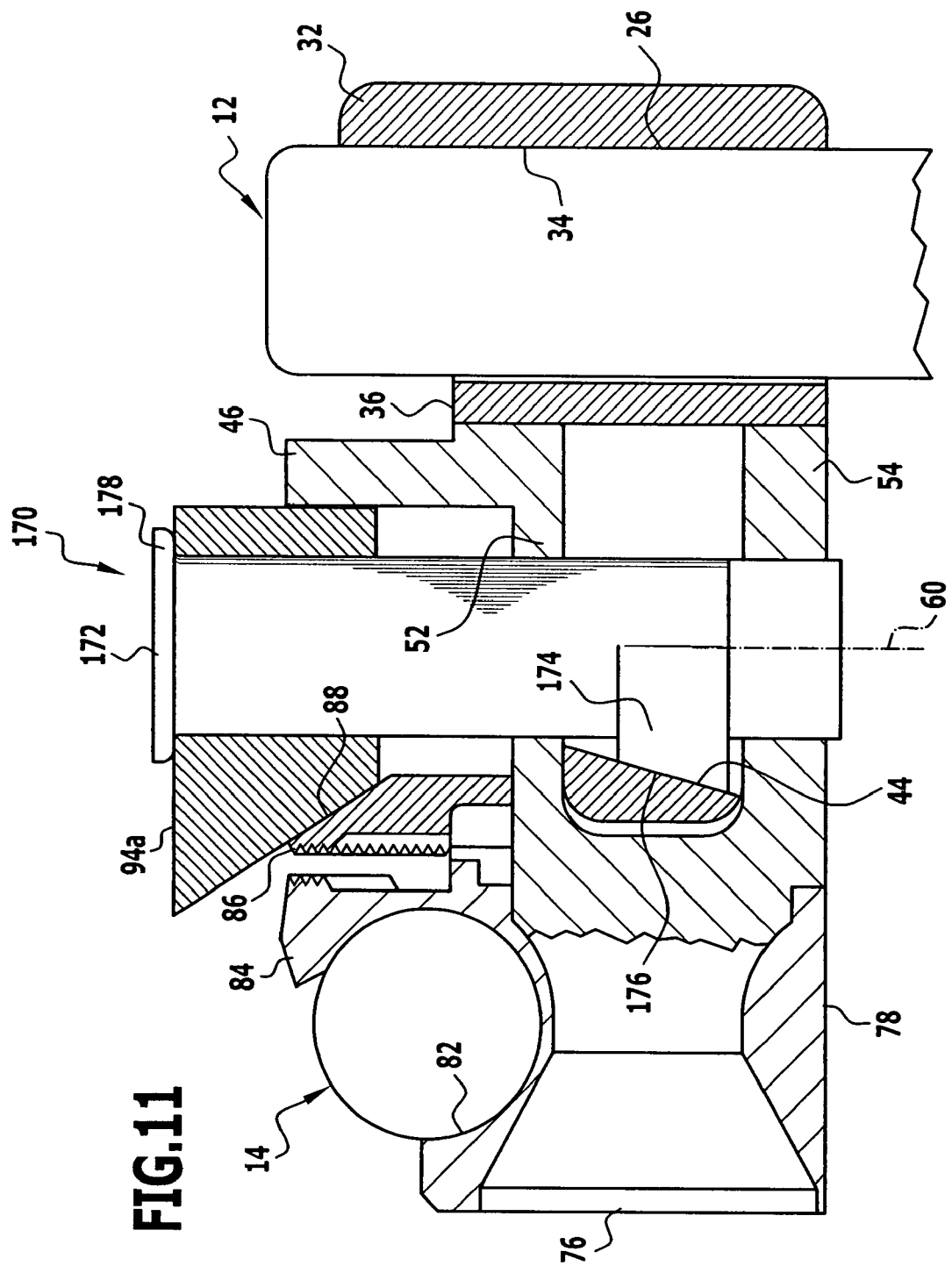
FIG. 11: shows a sectional view similar to FIG. 5 through a sixth embodiment of a fixation device.

A sixth embodiment of a clamping connector provided altogether with the reference numeral 170 is illustrated in FIG. 11. in comparison with the clamping connector 16, a rivet-like tensioning member 172 serves to transfer the clamping connector 170 from the adjusting position into the fixing position. Instead of the first clamping member 94, a clamping member 94a is provided which corresponds in its shape to the first clamping member 94 but has no internal thread. At the distal end of the tensioning member 172, located opposite the conical actuating surface section 44, a projection 174 corresponding to it is provided and this has a second slide-on surface 176 which abuts on the conical actuating surface section 44. The projection 174 can be designed in one piece with the tensioning member 172 or be connected securely to it. In order to transfer the clamping connector 170 from the adjusting position into the fixing position, the first clamping member 94a is pressed by a tensioning tool, which is not illustrated in detail, parallel to the longitudinal axis 60 in the direction towards the upper side wall 52 and the tensioning member 172 is drawn somewhat in the opposite direction at the same time. As soon as the connecting section 26 is secured in the connecting section receiving means 34 and the bar 14 in the bar receiving means 82 in a similar manner to that of the clamping connector 16, a head 178 of the tensioning member 172 is deformed in such a manner that the first clamping member 94a is secured in its position slid onto the actuating surface 88. A release of the clamping connector 170 is only possible by destroying the tensioning member 172. It is therefore possible with the clamping connector 170 to provide a one-time connection between the bone screw 12 and the bar 14 which can, however, no longer be released or readjusted.

Figure 12:
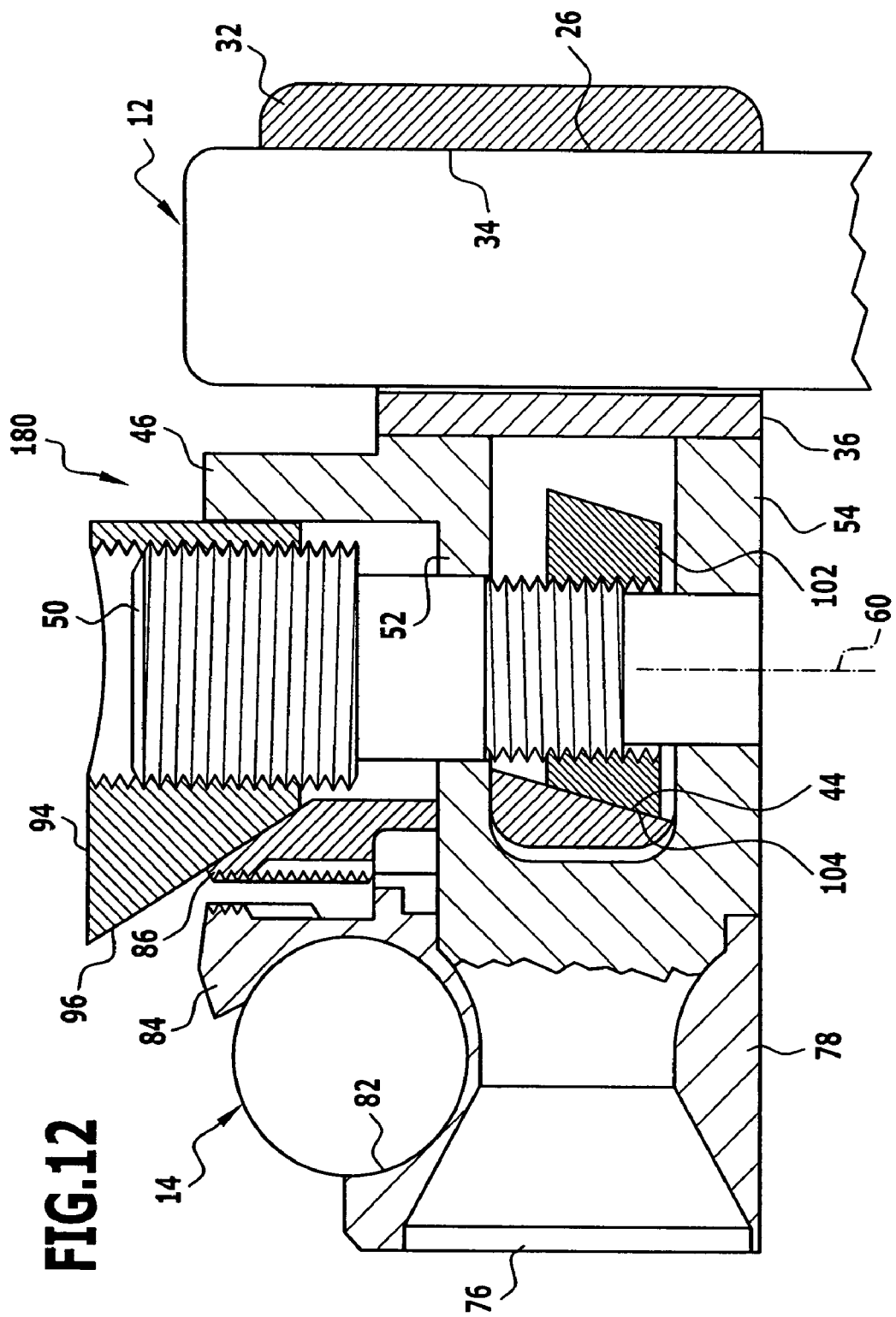
FIG. 12: shows a sectional view similar to FIG. 5 through a seventh embodiment of a fixation device.

In FIG. 12, a seventh embodiment of a clamping connector provided altogether with the reference numeral 180 is illustrated. The clamping connector 180 differs from the clamping connector 16 due to the fact that the clamping member 36 is not connected in one piece to the offset bridge 32, i.e., is not connected to it via a web. Otherwise, the construction corresponds to that of the clamping connector 16 and, therefore, also the principle mode of operation.

Figure 13:
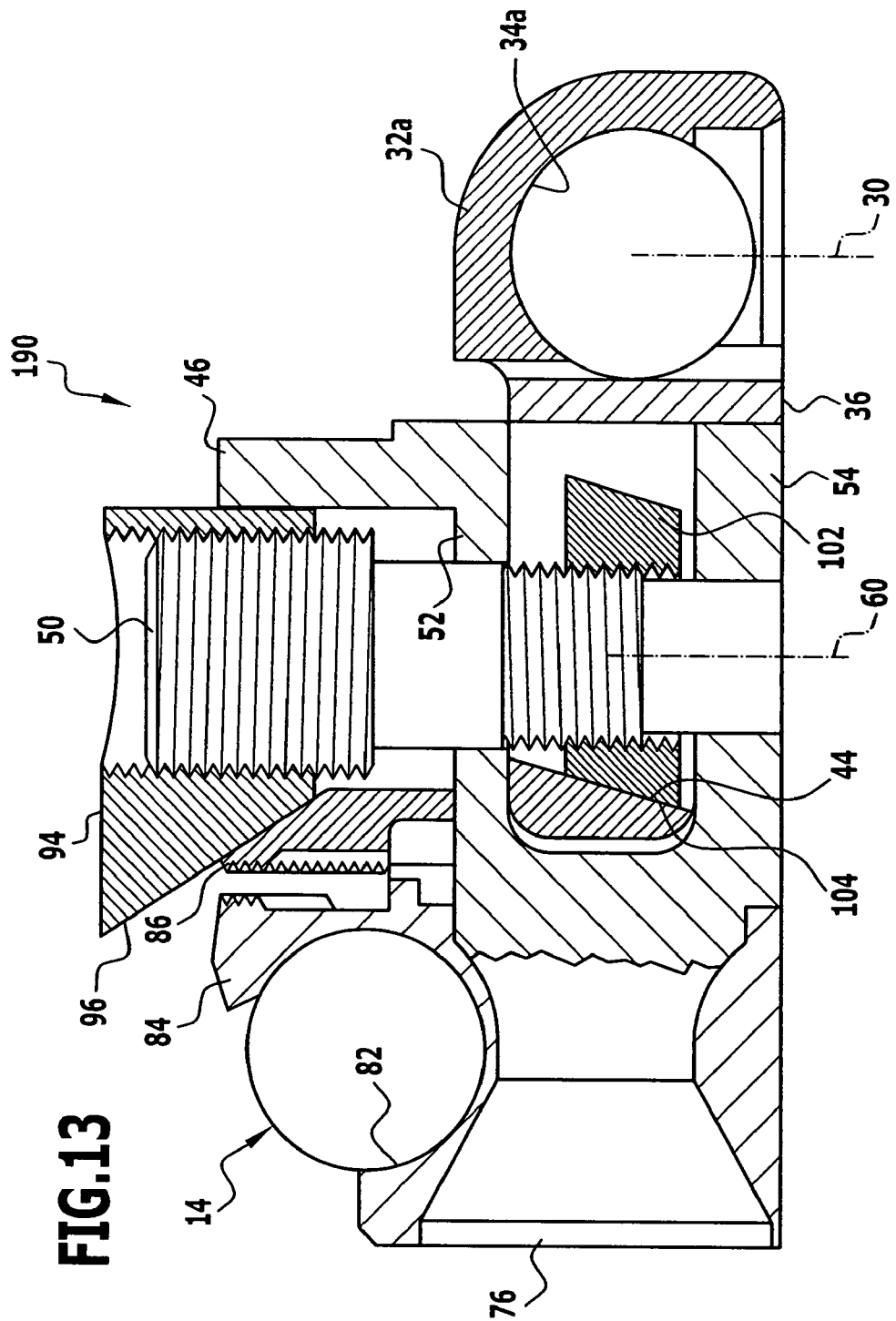
FIG. 13: shows a sectional view similar to FIG. 5 through an eighth embodiment of a fixation device.

Finally, an eighth embodiment of a clamping connector according to the invention and provided with the reference numeral 190 is illustrated in FIG. 13. It differs from the clamping connector 16 only as a result of the configuration of the connecting section receiving means 34 which is provided with the reference numeral 34a in the case of the clamping connector 190. It forms a hollow space in the shape of a spherical cap for accommodating an end, in the shape of a spherical cap, of a bone screw which is not illustrated in detail. The clamping connector 190 can, therefore, be used to secure a bar 14 on a bone screw with a spherical head. In an analogous way to all the other clamping connectors, the clamping connector 190 can be secured not only relative to the bar 14 but also relative to the bone screw not illustrated simply due to movement of the tensioning member 50.

With respect to the clamping connector 190 it is to be noted that the clamping connectors 120, 140, 150, 160, 170 and 180 described above may also be provided with a connecting section receiving means 34a in the shape of a spherical cap.

Furthermore, it is also possible to omit the clamping member 36 in the case of the clamping connectors 120, 140, 150, 160, 170 and 190, as described in conjunction with the clamping connector 180. In addition, the clamping member 86 can also be omitted in the case of the clamping connectors 120, 150, 160, 170, 180 and 190.

The invention claimed is:

1. An orthopedic fixation device for connecting a first anchoring element having a connecting section and being adapted to be anchored in or on a bone to a connecting element adapted to be connected to a second anchoring element adapted to be anchored in or on a bone, wherein the fixation device is movable relative to the connecting element and to the first anchoring element in an adjusting position and is adapted to be secured on the connecting element and on the first anchoring element in a fixing position, wherein a single tensioning member supported so as to be movable is provided for transferring the fixation device from the adjusting position into the fixing position and vice versa, the fixation device comprising at least one first supporting element and the tensioning member supported on the at least one first supporting element so as to be rotatable relative to the first supporting element, the fixation device having a connecting section receiving means for accommodating the connecting section, said receiving means corresponding to the connecting section, the connecting section receiving means rotatable about a first axis of rotation relative to the connecting element receiving means, the fixation device comprising a first supporting element supporting the connecting element receiving means and a second supporting element supporting the connecting section receiving means and being supported on the first supporting element so as to be rotatable about a first axis of rotation in the adjusting position, and the second supporting element supported on the connecting section so as to be rotatable about a second axis of rotation in the adjusting position.

2. A fixation device as defined in claim 1, wherein the tensioning member is supported relative to the first supporting element so as to be translatable.

3. A fixation device as defined in claim 1, wherein in the adjusting position the connecting element is displaceable relative to the first anchoring element parallel to itself towards or away from the first anchoring element.

4. A fixation device as defined in claim 1, wherein the fixation device has a connecting element receiving means for accommodating the connecting element, said receiving means corresponding to the connecting element.

5. A fixation device as defined in claim 1, wherein a first clamping device is provided for clampingly securing the fixation device on the connecting element in the fixing position, wherein a second clamping device is provided for clampingly securing the fixation device on the first anchoring element in the fixing position and wherein the first clamping device comprises the tensioning member and wherein the second clamping device comprises the tensioning member.

6. A fixation device as defined in claim 5, wherein the first clamping device comprises a first clamping element having a first slide-on surface abutting directly or indirectly on a first actuating surface of a first clamping member of the first supporting element and wherein as a result of movement of the tensioning member the first clamping element is movable in such a manner that the first slide-on surface is able to slide on the first actuating surface and reduce a cross section of the connecting element receiving means in such a manner that the connecting element is adapted to be secured in the connecting element receiving means.

7. A fixation device as defined in claim 6, wherein a first force transfer member arranged between the first slide-on surface and the first actuating surface is provided for transferring a force from the first clamping element to the first clamping member.

8. A fixation device as defined in claim 6, wherein the first slide-on surface and the first actuating surface are inclined relative to the first axis of rotation.

9. A fixation device as defined in claim 6, wherein the first clamping element is designed in the shape of a cone.

10. A fixation device as defined in claim 6, wherein the first clamping element and the tensioning member are designed in two parts.

11. A fixation device as defined in claim 6, wherein the tensioning member has a first external thread section, wherein the first clamping element has a first internal thread section corresponding to the first external thread section and wherein the first clamping element is displaceable parallel to itself as a result of rotation of the tensioning member about its longitudinal axis.

12. A fixation device as defined in claim 5, wherein the second clamping device comprises a second clamping element having a second slide-on surface abutting directly or indirectly on a second actuating surface of the second supporting element, and wherein as a result of movement of the tensioning member the second clamping element is movable in such a manner that the second slide-on surface slides on the second actuating surface and a second clamping member limiting the connecting section receiving means in sections is movable in such a manner that a cross section of the connecting section receiving means is able to be reduced such that the connecting section of the first anchoring element is adapted to be secured in the connecting section receiving means.

13. A fixation device as defined in claim 12, wherein the second clamping element is designed at least partially in the shape of a cone.

14. A fixation device as defined in claim 12, wherein the second clamping element and the tensioning member are designed in two parts.

15. A fixation device as defined in claim 12, wherein in the fixing position the second supporting element is supported on the connecting section via the second clamping member.

16. A fixation device as defined in claim 12, wherein the second clamping member and the second supporting element are designed in two parts.

17. A fixation device as defined in claim 1, wherein the tensioning member forms a bearing shaft defining the first axis of rotation.

18. A fixation device as defined in claim 1, wherein the first and the second axes of rotation extend parallel to one another.

19. A fixation device as defined in claim 1, wherein the connecting section forms the proximal end of the first anchoring element or is arranged in the area of the proximal end of the first anchoring element.

20. A fixation device as defined in claim 1, wherein the tensioning member has a tool receiving means for accommodating a tensioning tool and wherein the tensioning member is movable with the tensioning tool.

21. An orthopedic fixation system comprising at least two anchoring elements adapted to be anchored in or on a bone, at least one connecting element for connecting the at least two anchoring elements and at least one orthopedic fixation device for connecting the at least one connecting element to a connecting section of one of the at least two anchoring elements, wherein the at least one orthopedic fixation device is a fixation device as defined in claim 1.

22. A fixation system as defined in claim 21, wherein the connecting section is designed so as to be thread-free and is cylindrical or essentially cylindrical in shape.

23. A fixation system as defined in claim 21, wherein each of the at least two anchoring elements comprises a screw thread section forming its distal end for screwing into a bone.

24. A fixation system as defined in claim 21, wherein each of the at least two anchoring elements comprises a hook forming its distal end for anchoring said anchoring element in a bone.

25. A fixation system as defined in claim 21, wherein the connecting element is a bar or a connecting plate with at least one bar-like plate section.

26. An orthopedic fixation device for connecting a first anchoring element having a connecting section and being adapted to be anchored in or on a bone to a connecting element adapted to be connected to a second anchoring element adapted to be anchored in or on a bone, wherein the fixation device is movable relative to the connecting element and to the first anchoring element in an adjusting position and is adapted to be secured on the connecting element and on the first anchoring element in a fixing position, wherein a single tensioning member supported so as to be movable is provided for transferring the fixation device from the adjusting position into the fixing position and vice versa, the fixation device comprising at least one first supporting element and the tensioning member supported on the at least one first supporting element so as to be rotatable relative to the first supporting element,
- the fixation device having a connecting section receiving means for accommodating the connecting section, said receiving means corresponding to the connecting section,
- the connecting section receiving means rotatable about a first axis of rotation relative to the connecting element receiving means,
- the fixation device comprising a first supporting element supporting the connecting element receiving means and a second supporting element supporting the connecting section receiving means and being supported on the first supporting element so as to be rotatable about a first axis of rotation in the adjusting position,
- the second clamping device comprising a second clamping element having a second slide-on surface abutting directly or indirectly on a second actuating surface of the second supporting element, and as a result of movement of the tensioning member the second clamping element is movable in such a manner that the second slide-on surface slides on the second actuating surface and a second clamping member limiting the connecting section receiving means in sections is movable in such a manner that a cross section of the connecting section receiving means is able to be reduced such that the connecting section of the first anchoring element is adapted to be secured in the connecting section receiving means, wherein the second slide-on surface and the second actuating surface are inclined relative to the first axis of rotation.

27. An orthopedic fixation system comprising at least two anchoring elements adapted to be anchored in or on a bone, at least one connecting element for connecting the at least two anchoring elements and at least one orthopedic fixation device for connecting the at least one connecting element to a connecting section of one of the at least two anchoring elements, wherein the at least one orthopedic fixation device is a fixation device as defined in claim 26.

28. An orthopedic fixation device for connecting a first anchoring element having a connecting section and being adapted to be anchored in or on a bone to a connecting element adapted to be connected to a second anchoring element adapted to be anchored in or on a bone, wherein the fixation device is movable relative to the connecting element and to the first anchoring element in an adjusting position and is adapted to be secured on the connecting element and on the first anchoring element in a fixing position, wherein a single tensioning member supported so as to be movable is provided for transferring the fixation device from the adjusting position into the fixing position and vice versa, the fixation device comprising at least one first supporting element and the tensioning member supported on the at least one first supporting element so as to be rotatable relative to the first supporting element,
- the fixation device having a connecting section receiving means for accommodating the connecting section, said receiving means corresponding to the connecting section,
- the connecting section receiving means rotatable about a first axis of rotation relative to the connecting element receiving means,
- the fixation device comprising a first supporting element supporting the connecting element receiving means and a second supporting element supporting the connecting section receiving means and being supported on the first supporting element so as to be rotatable about a first axis of rotation in the adjusting position,
- wherein the connecting element receiving means is supported on the first supporting element so as to be rotatable about a third axis of rotation and wherein the third axis of rotation extends transversely to a longitudinal axis of the connecting element receiving means.

29. A fixation device as defined in claim 28, wherein the third axis of rotation extends transversely to the first and/or to the second axis of rotation.

30. An orthopedic fixation system comprising at least two anchoring elements adapted to be anchored in or on a bone, at least one connecting element for connecting the at least two anchoring elements and at least one orthopedic fixation device for connecting the at least one connecting element to a connecting section of one of the at least two anchoring elements, wherein the at least one orthopedic fixation device is a fixation device as defined in claim 28.

\* \* \* \* \*